United States Patent
Hendrickson et al.

(10) Patent No.: US 9,751,814 B2
(45) Date of Patent: Sep. 5, 2017

(54) PERSISTENT, TARGETED, OPTIMIZED, SOIL AMENDMENT COMPOSITION AND METHOD

(71) Applicant: AQUASMART ENTERPRISES, LLC, Lubbock, TX (US)

(72) Inventors: Calder Hendrickson, Lubbock, TX (US); Todd Naff, Wolfforth, TX (US)

(73) Assignee: AQUASMART ENTERPRISES, LLC, Lubbock, TX (US)

( * ) Notice: Subject to any disclaimer, the term of this patent is extended or adjusted under 35 U.S.C. 154(b) by 0 days.

(21) Appl. No.: 15/351,794

(22) Filed: Nov. 15, 2016

(65) Prior Publication Data

US 2017/0057882 A1    Mar. 2, 2017

Related U.S. Application Data

(62) Division of application No. 14/575,877, filed on Dec. 18, 2014, now Pat. No. 9,527,781.

(60) Provisional application No. 61/918,277, filed on Dec. 19, 2013.

(51) Int. Cl.
| | |
|---|---|
| *C05G 3/04* | (2006.01) |
| *C05G 3/02* | (2006.01) |
| *C09K 17/00* | (2006.01) |
| *C09K 17/16* | (2006.01) |
| *A01C 1/04* | (2006.01) |

(Continued)

(52) U.S. Cl.
CPC .............. *C05G 3/04* (2013.01); *A01C 1/046* (2013.01); *A01N 25/26* (2013.01); *C05G 3/0011* (2013.01); *C05G 3/0029* (2013.01); *C05G 3/0052* (2013.01); *C05G 3/02* (2013.01); *C09K 17/00* (2013.01); *C09K 17/16* (2013.01)

(58) Field of Classification Search
CPC .......... C05G 3/04; C05G 3/02; C05G 3/0011; C05G 3/0052; C09K 17/00; C09K 17/16; A01C 1/046
See application file for complete search history.

(56) References Cited

U.S. PATENT DOCUMENTS

| | | |
|---|---|---|
| 2,690,388 A | 9/1954 | Hale |
| 2,991,267 A | 4/1957 | Bean |
| 2,967,789 A | 1/1961 | Hoyt |

(Continued)

FOREIGN PATENT DOCUMENTS

| | | |
|---|---|---|
| WO | WO 8501736 | 4/1985 |
| WO | WO2009102565 | 8/2009 |

OTHER PUBLICATIONS

Drill & Fill Manufacturing. Turf Tractor Specifications. http://www.drillandfillmfg.com/tractor.html. Accessed May 27, 2008.

(Continued)

*Primary Examiner* — Wayne Langel
(74) *Attorney, Agent, or Firm* — Pate Baird, PLLC

(57) ABSTRACT

A material for optimizing and maintaining at least one of water, nutrients, biocides, and other protectant or growth supporting chemicals in natural soils by decreasing leaching, evaporation, and volatility through application of agglomerated granules (prills) formed of engineered hydrating particles, a binder, nutrients, and protectants to the soil. Typical application is by applying prills simultaneously with seeds when drilled, broadcast, or otherwise distributed.

20 Claims, 12 Drawing Sheets

(51) Int. Cl.
*C05G 3/00* (2006.01)
*A01N 25/26* (2006.01)

(56) References Cited

U.S. PATENT DOCUMENTS

| | | | |
|---|---|---|---|
| 3,648,631 A | 3/1972 | Fiedler et al. | |
| 3,973,355 A | 8/1976 | McKenzie | |
| 4,195,010 A | 3/1980 | Russell | |
| 4,247,331 A | 1/1981 | Hamlin | |
| 4,579,578 A | 4/1986 | Cooke | |
| 4,579,587 A | 4/1986 | Grant et al. | |
| 4,762,545 A * | 8/1988 | Youssef | C05G 3/0052 71/27 |
| 5,394,812 A | 3/1995 | Dunning et al. | |
| 5,450,985 A | 9/1995 | Meuleman | |
| 5,554,446 A | 9/1996 | Minder et al. | |
| 5,794,550 A | 8/1998 | Chadwick | |
| 5,951,978 A | 9/1999 | Red'kina | |
| 6,329,319 B1 | 12/2001 | Puglisi et al. | |
| 6,395,051 B1 | 5/2002 | Arnold et al. | |
| 6,669,752 B2 | 12/2003 | Arnold et al. | |
| 6,703,469 B2 * | 3/2004 | Sanders | C05G 3/0029 504/271 |
| 6,884,754 B1 | 4/2005 | Schlatter et al. | |
| 7,244,492 B2 | 7/2007 | Sinclair et al. | |
| 7,504,445 B2 | 3/2009 | Collin | |
| 7,635,404 B1 * | 12/2009 | Devic | A01N 25/12 71/11 |
| 7,726,070 B2 | 6/2010 | Thrash | |
| 7,989,391 B2 | 8/2011 | Tang et al. | |
| 8,196,346 B2 | 6/2012 | Thrash | |
| 8,341,881 B2 | 1/2013 | Thrash | |
| 8,453,377 B2 | 6/2013 | Thrash et al. | |
| 8,510,986 B2 | 8/2013 | Thrash | |
| 8,881,453 B2 | 11/2014 | Hendrickson et al. | |
| 8,931,209 B2 | 1/2015 | Hendrickson et al. | |
| 9,174,885 B2 * | 11/2015 | Taulbee | C05C 1/02 |
| 9,527,781 B2 * | 12/2016 | Hendrickson | C05G 3/04 |
| 2002/0049291 A1 * | 4/2002 | Sanders | C05D 9/02 526/271 |
| 2003/0046865 A1 | 3/2003 | Nishiyama | |
| 2004/0069032 A1 * | 4/2004 | Krysiak | A01C 1/046 71/27 |
| 2005/0005869 A1 | 1/2005 | Fritter et al. | |
| 2006/0047068 A1 | 3/2006 | Doane et al. | |
| 2006/0078682 A1 | 4/2006 | McDaniel et al. | |
| 2006/0240983 A1 | 10/2006 | Yamaguchi | |
| 2007/0093387 A1 | 4/2007 | Sumi et al. | |
| 2008/0230223 A1 | 9/2008 | McCrary et al. | |
| 2008/0234129 A1 | 9/2008 | Asrar et al. | |
| 2011/0212834 A1 | 9/2011 | Andersch et al. | |

OTHER PUBLICATIONS

Drill & Fill Manufacturing. DF24—Drill & Fill Aerator Head Specifications. http://www.drillandfillmfg.com/drillfill.html. Accessed May 27, 2008.

Drill & Fill Manufacturing. D60—Drill Aerator Head Specifications. http://www.drillandfillmfg.com/drill.html. Accessed May 27, 2008.

Drill & Fill Manufacturing. Drill & Fill Aerification. http://www.drillandfillmfg.com/options.html. Accessed May 27, 2008.

Hogentogler & Co., Inc, Sieves: ASTM E-11 / AASHTO T-27. M-92. http://www.hogentogler.com/sieves/200mm_metric_sieves.htm. Accessed Dec. 11, 2007.

Graden USA, Inc. CSI Contour Sand Injection Specifications. http://www.gradenusa.com/_Sand_Injection.php. Accessed May 27, 2008.

Silica Fume Association. "What is Silica Fume?" http://www.silicafume.org/general-silicafume.html. Accessed May 27, 2008.

AZ Materials. Silica—Fumed Silica (Silicon Dioxide). http://www.azom.com/details.asp?ArticleID=1386. Accessed May 27, 2008.

DryJect: Soil Amendments. http://www.dryject.com/dryject/profile.cfm. Accessed May 27, 2008.

DryJect: How it Works. http://www.dryject.com/dryjet/howitworks/index.cfm. Accessed May 27, 2008.

* cited by examiner

No Water

Initial Water – 20 mL

2 Minutes – 20 mL

3 Minutes – 20 mL

5 Minutes – 40 mL

30 Minutes – 40 mL

50 Minutes – 40 mL

50 Minutes – 40 mL

PERSISTENT, TARGETED, OPTIMIZED, SOIL AMENDMENT COMPOSITION AND METHOD

RELATED APPLICATIONS

This patent application; is a divisional (continuation) of U.S. patent application Ser. No. 14/575,877, filed Dec. 18, 2014; which claims the benefit of U.S. Provisional Patent Application No. 61/918,277, filed on Dec. 19, 2013, both of which are hereby incorporated herein by reference. This patent application also hereby incorporates herein by reference U.S. Pat. No. 8,881,453, issued Nov. 11, 2014, U.S. Pat. No. 7,726,070, issued Jun. 1, 2010, U.S. Pat. No. 8,196,346, issued Jun. 12, 2012, and U.S. Pat. No. 8,453,377, issued Jun. 4, 2013.

BACKGROUND

Field of the Invention

This invention relates to agriculture and horticulture, more particularly, to novel systems and methods for amending soil by delivering materials thereinto for to maintain better introduction and maintenance of hydration, nutrients, and protectants in the soil.

Background Art

Watering schedules, rain, sunshine, and other weather, with consequent soil moisture, soil warmth, light, and air temperature vary greatly over periods of days during a planting season. Likewise, soils may vary so drastically that any or all of the foregoing conditions may produce different results for various types of soils.

Husbanded crops of Agriculture and Horticulture rely on water as a transport mechanism to draw nutrients and protectants from the ground into the plants through roots and out into stems, leaves, and so forth. Likewise, water acts as a transpiration cooling mechanism by evaporation out through the leaves and other foliage of a plant. Thus, the health of the plants depends upon access to water, nutrients, protective chemicals such as pesticides and protectants (e.g., biocides or pathogencides acting against insects, microbes, fungi, weeds, etc.).

Many parts of the United States receive little rainfall; thus irrigation systems are required in many parts of the country to produce adequate yields. Irrigation or periodic rainfall is often required to have a healthy plant. One major issue is plants may dwell for an extended period without additional water, which inhibits germination, growth, and yields of plants. This is greatly determined by the overall soil structure of clay, silt, and sand in the soil.

Different types of soils perform their functions differently. In particular, sandy soils and the like pass water, nutrients, and protectants too freely. Likewise clay soils tend to hold water, but yet not permit the water to distribute therethroughout. In general, soil may be improved on a small scale by amending, the addition of organic matter such as peat moss. However, standard practice for growers does not allow for the application of amendments to soils. On a large production agriculture scale, soils are typically only improved by plowing under certain plants selected for addition of organic matter. Likewise, waste materials from corrals, grain stalks (straw) and the like may be plowed into tracts of land in order to improve their organic content and their capacity to hold water, nutrients, and protectants for use by the plants.

Gelatin is naturally occurring polymer. Gelatin binds with water to form a "gel." The existence of naturally occurring polymers such as gelatin has been augmented by the development of synthetic polymers. Such polymers as SAPs, polyacrylates, and polyacrylamides, and other similar gels have been used for different types of binding processes.

Herein SAP refers to a super absorbent polymer that does not dissolve in water. Rather, due to internal chemistry, such as cross-linking, particles of SAP do not dissolve, but swell as spherical entities that maintain their integrity and chemical structure, albeit while holding many times (e.g., hundreds of times) the weight of the actual polymer in absorbed water. Some SAPs may include acrylamides, polyacrylamides, and other products of acrylic acid chemistry. However, they are considered herein to be those polymers that absorb many times their weight in water, while remaining insoluble in water, and therefore maintain the distinctiveness and integrity of each particle thereof.

In contrast, PAM or polyacrylamide, when not designated as a SAP, is a water soluble polymer or co-polymer. It also absorbs water. However, absent the crosslinking of SAPs, it will dissolve in water.

Gels typically are formed by comparatively "long-chain" or high-molecular-weight polymers and thus are often durable in the face of erosive actions such as water running over them. Accordingly, gels such as polyacrylate and polyacrylamides have been used to treat surfaces of ground in order to minimize erosion by passing of water thereover. These gels can retain up to 400× their weight in water in the gel matrix.

In past years, these polymer gels, both water soluble and insoluble, used in the soil can improve plant nutrition and moisture conditions. Many polymers originally developed for agriculture have not attracted widespread attention. Studies found that these gels used in agriculture for improving soils' physical properties may promote seed germination and emergence, improve the survival rate of seedlings, reduce the need for irrigation, and improve the use of nutrients and chemicals.

One of the many reasons the agricultural industry has not adopted the use of gels in farming is that application rates required to demonstrate benefits are comparatively high, actually cost prohibitive for the farmer. Studies have shown benefits of reducing irrigation, fertilizers, and chemicals in crops, while applying 20-30 lbs. of gel per acre.

It would be an advancement in the art if a grower could apply less gel per acre at economical rates that work for the grower.

Higher clay soils can retain larger amounts of water, however, when they begin to dry, compaction is a very serious issue, which leads to very little porosity and oxygen for the plant, and will lead to run-off and erosion of water, nutrients, and protectants. Sandy soils result in quick leaching of water, nutrients, and protectants, as their holding capacity is very limited.

Thus, it would be a great advancement in the art to provide a composition and methods whereby to automatically deliver and store within various soil types a mechanism to absorb, carry, hold, and re-deliver water, nutrients (e.g., fertilizer), protectants (e.g., biocides/pathogencides), and other soil amendments to plants over extended periods of time. It would be an advance to release these materials in a region of greatest utility over time while resisting loss, evaporation, volatility, migration away, and the like, which occur frequently for materials supporting plant growth in existing soils.

Granules such as nutrients (fertilizer) and protectants (pathogencides) are currently being applied in agricultural production via large broadcast systems or directly in-furrow with a drill or air planter. It would be an advancement in the art of farming if a grower could also apply, using their existing equipment, a similar sized granule (similar to seed or fertilizer) containing protectants and nutrients that could amend and enhance the soil (e.g., clay, silt, and sand).

It would be a further advance to optimize the use of the water, nutrients, and protectants being used in the field. This would be a further advance if also optimizing the materials and rates used for amending the soils to better absorb, carry, hold, and ultimately deliver such components back to the plant, which would decrease the loss of water, nutrients, and protectants from run-off, leaching, or both.

It would be a great advancement and simplification if done in such a manner and configuration that the grower would be able to take such advancement and integrate it easily into existing farming methods. The conglomeration of one or all of a hydrophilic material, nutrient, and protectant made into a granule of similar size, shape, and density as existing granules being used by growers would advance the overall art of growing crops like corn, soybeans, wheat, cotton, sunflowers, and the like.

Existing granules being used in this art can range in granule size. Some granules may have a comparatively greater density (mass per unit volume), specific weight (weight per unit volume), or specific gravity (density compared to that of water). Others may have comparatively lesser values of such. The term "density" will be used herein to represent the performance for all the above.

BRIEF SUMMARY OF THE INVENTION

In view of the foregoing, in accordance with the invention as embodied and broadly described herein, a method and composition are shown for amending soil. One advance in the art is to provide a process or method of delivering soil amendments into soils, near seeds or roots to be most effective. A further advance is to use an agglomeration to form granules (prills) of one or all of a hydrophilic material, nutrients, and protectants to be used with the existing application of other fertilizers and chemical granules. The prills are calculated, formulated, and distributed to optimize the water (in both irrigated and dry land fields) and the normal nutrient and chemical regimen by amending the soils, while not changing the growers' application system.

In one embodiment of the composition, a mixture of similarly sized materials (hydrating agent, nutrients, protectant, soil modifiers such as lime, gypsum, acids, alkalines, etc., or other materials) are all coated with a binder and formed into granules/prills. One embodiment of the composition and method in accordance with the present invention includes small (5 to 400) micron particles of a hydrophilic material formed as a granule with a binder, then coating it with one or more outer layers of hydrophilic material mixed with other amendments and a binder. These outer layers of hydrophilic material may include nutrients, protectants, or other materials. Each may be in a core granule, the first layer, or other layer. Distributing (e.g., spreading, broadcasting, sowing, planting, etc.) the coated granule or prill (e.g., agglomerated amendment of hydrophilic powder, chemicals, biocides, soil modifiers, or any combination thereof, etc.).

Various protectants (e.g., biocides, pathogencides, pesticides, fungicides, herbicides) hydration aids, nutrients and combinations thereof may be added as powders bonded, by the binder together with the hydrophilic material or to it. On the other hand, any protectant or nutrient that may be mixed or dissolved into the hydration binder may be distributed therewith. In certain embodiments, the material of the powders will sooner or later, as designed, separate from the attachment in the prill. With subsequent hydration absorbents will absorb water and soluble nutrients and biocides.

Absorbents may then slowly release to the plant the protectants, nutrients, or both directly to adjacent roots. Materials in prills may be extended by "fillers" or in other words "extenders." Dry flow agents and any other appropriate excipients may be applied in forming the granule or prill to match the overall requirement for active hydrophilic material, nutrient, protectant, or their combination.

Also, various other chemicals or structural amendments may be included in prills in accordance with the invention. For example, lime, gypsum, sulfurous acid, and the like may modify soil chemistry or structural constitution to aid in the processes of water retention, remediation, transport, or the like. Such materials may remediate acidity, alkalinity, salt, or other chemistry of soils.

Thus, soil amendment materials that aid the soil in becoming a better host for plants may be added, even though they are not taken up directly by plants. Any materials may be added to prills as separate particles, as chemicals absorbed into polymers, or otherwise as part of the mix of materials forming the prills. These added materials may then be introduced into the soil to amend chemical or mechanical characteristics of the soil, to be taken up by plants, to protect the soil for the benefit of plants, to feed plants, to protect plants within their own structures, or any combination thereof.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
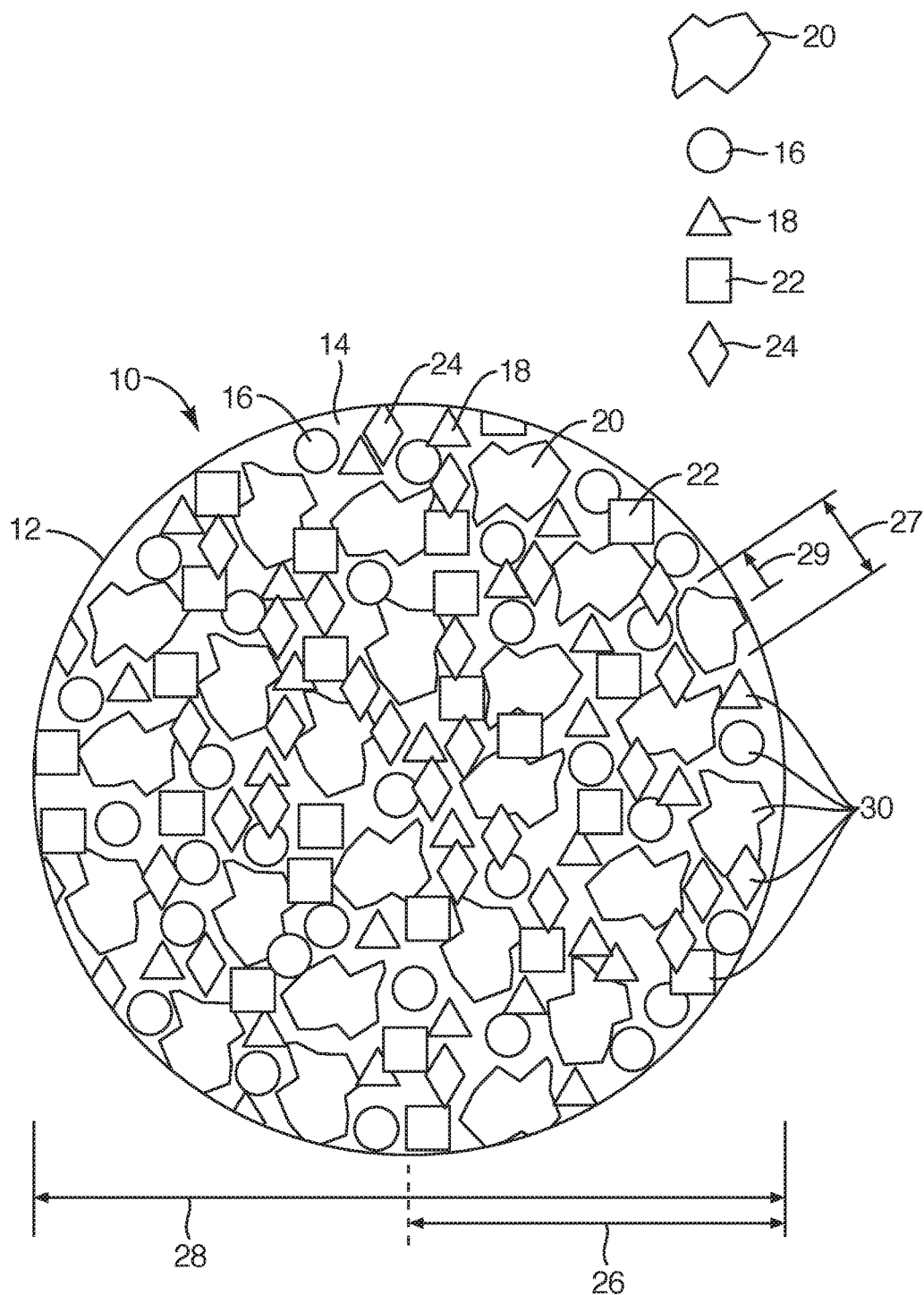
FIG. 1 is a schematic diagram of one embodiment of a prill, in accordance with the invention, including a binder holding together nutrients, biocides, and absorbents.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Reference numerals are used with respect to various steps and processes and components of devices in composition described hereinbelow. A trailing letter behind the reference number corresponding to an item refers to a specific instance of the numbered item.

It will be proper herein to speak of a reference numeral with no trailing letter, or a reference numeral with a trailing letter. The reference numeral alone indicates a component of that designation. A trailing letter indicates a specific instance, which may be necessary or useful for clarity in speaking of a specific instance of the item designated by the numeral. Thus, it is not necessary that every reference numeral be used alone, nor that every reference numeral with a trailing letter be used herein for clarity.

Referring to FIG. 1, and FIGS. 1-15 generally, a prill 10 may be thought of as a granule 10 having a shape, that will typically be approximately spherical in nature. Nevertheless, a prill 10 may be formed by any one of several methods. For example, prills may be formed by disc pelletizing, sometimes known as pan granulation, or paddle mixing, sometimes referred to as a pug mill, or other methods. The prill 10 may be formed by drum granulation in a "drum pelletizer." Other devices include a pin mixer. Likewise, briquetting is another feasible method for forming a prill 10.

Briquetting represents a casting or forming process for the mixture of constituents. The other methods, like disc pelletizing, constitute agglomeration processes. Agglomeration will tend to produce prills 10 that approximate spheres. In contrast, briquetting can be used to form a prill 10 in any particular shape. For flow, delivery, measurement, volumetric efficiency, and so forth, a spherical shape may be most suitable.

As a practical matter, a seed drill must accommodate seed. Seed is not necessarily round. Seeds have a variety of irregular shapes. A seed drill may include a hopper (or several) for delivery of seed with another (corresponding) hopper reserved for other materials, such as fertilizer. Prills 10 in accordance with the invention may be mixed with seed. However, they are preferably delivered from their own dedicated hopper into the ground simultaneously with the seed, each from its own source, in one or more delivery conduits into the ground.

In the illustrated embodiment, the surface 12 is actually an outer surface 12, formed by a binder 14 holding together various powdered or particulate nutrient 16, biocides 18, and absorbents 20. Typical nutrients may include, for example, nitrogen and its sources, potassium and compositions thereof, phosphorous, zinc, manganese, magnesium, sulfur, boron, calcium, silicon, chlorine, iron, copper, molybdenum, nickel, selenium, and sodium. Sizes may be from about 5 to about 400 microns in effective diameter. A range of 100 to 200 microns works well. Particles may have a comparatively narrow or broad range of sizes of any material.

Typical biocides 18 may be referred to as protectants 18 or pathogencides 18. In general, a biocide 18 is anything that acts against a biological organism, whether plant or animal, whether macroscopic, such as insects, or microscopic, such as bacteria, mold, microbes, fungi, or the like. Thus, in general, biocides 18 may include protectants 18 such as herbicides 18, insecticides 18, fungicides 18, other pesticides 18 against microscopic or macroscopic pests, and so forth. Similarly, nutrients may include any of the chemicals, metals, catalysts, growth enhancers, growth regulation, or foregoing materials. Each is typically bound up in some source material, a compound of the nutrient, which compound will deliver, based on certain chemical reactions or processes, the key nutrient to a plant.

The absorbents 20 may be water soluble or insoluble. Applicants have found that water-soluble nutrients have certain benefits documented in other patent applications that have been incorporated herein by reference. Meanwhile, non-dissolving or insoluble absorbents have also been shown to be extremely useful. Nevertheless, they have difficulties with their application rates, costliness, and so forth.

In a composition and method in accordance with the invention, the absorbents 20 may be water-soluble absorbents 20, such as acrylamides of various types and acrylate-based polymers, copolymers, and so forth. Likewise, various other super absorbent polymers (SAP) may also be used, which are insoluble in water. These tend to remain longer in-situ, and thus may have greater longevity even within a single season. This may be significant in the operation of the prill 10 as a delivery mechanism for nutrients that should disperse, but not leach away.

For example, a prill 10 in accordance with the invention may dissolve its binder 14 upon application of water to a row crop in a furrow where the prill 10 has been sown with seed. Thus, the binder 14 may dissolve, releasing the powdered or particulate nutrients 16, biocides 18, and absorbents 20.

In turn, as the nutrients 16 and biocides 18 dissolve with the water, they are absorbed with that water into the absorbent 20. Thus, they are released and immediately captured by the same transport mechanism, diffusion through (and diffusion of) water from irrigation or rain into the soil, into the absorbent 20. Components 16, 18 are thereby captured for future use of a nearby plant root, rather than leaching away.

Typical insecticides 22 or other pesticides 22 may be thought of as specific biocides 18 in a specific instance directed to fauna, animal kingdom actors. Meanwhile, herbicides 24 may be thought of as specific biocides 18 directed to flora or plant materials, such as weeds, other herbs, any competing plant variety, old volunteer crops, and so forth.

Likewise, molds, fungi, and certain other micro organisms, may be thought of as flora or plant-kingdom pestilence.

In one embodiment of the composition, a mixture of similarly sized materials (hydrating agent, nutrients, protectant, soil modifiers such as lime, gypsum, acids, alkalines, etc., or other materials) may be coated with a binder and formed into granular prills to be distributed (e.g., spread, broadcast, sown, drilled, injected, planted, etc.). Each may include any one or more constituent in the coated granule or prill (e.g., agglomerated amendment, whether including hydrophilic powder, other hydration aid, biocides, pathogencides, pesticides, fungicides, herbicides, other chemicals, lime, gypsum, acid, alkali, other soil modifiers, or any combination thereof, etc.).

Certain of the foregoing may be mixed or dissolved into the hydration binder, hydrating polymer, other binder, or a combination. In certain embodiments, the material of the powders (small constituent particles of the prill) will sooner or later, as designed, separate from the attachment in the prill. With subsequent hydration, absorbents may absorb water and soluble nutrients and biocides.

Absorbents may then slowly release to the plant the protectants, nutrients, or both directly to adjacent roots. Materials in prills may be extended by "fillers" or in other words "extenders." Dry flow agents and any other appropriate excipients may be applied in forming the granule or prill to match the overall requirement for active hydrophilic material, nutrient, protectant, or their combination.

Various chemicals or structural amendments that may be included in prills, such as lime, gypsum, sulfurous acid, and the like may modify soil chemistry or structural constitution to aid in the processes of water retention, remediation, transport, or the like. Such materials may remediate acidity, alkalinity, salt, or other chemistry of soils.

Thus, soil amendment materials that aid the soil in becoming a better host for plants may be added, even though they are not taken up directly by plants. Any materials may be added to prills as separate particles, as chemicals absorbed into polymers, or otherwise as part of the mix of materials forming the prills. These added materials may then be introduced into the soil to amend chemical or mechanical characteristics of the soil, to be taken up by plants, to protect the soil for the benefit of plants, to feed plants, to protect plants within their own structures, or any combination thereof.

Each prill 10 will typically have a radius 26 measured from its center to its outer surface 12, which thereby defines a diameter 28 across the full extent of the prill 10. A diameter 28 may be defined for any cross-section. Typically, agglomeration processes for forming prills 10 will tend to form approximately spherical shapes. Thus, the diameter 28 may be an actual diameter of a spherical object.

Nevertheless, in certain instances, shapes may not necessarily be perfectly round. A non-round shape may still have an effective radius 26 and effective diameter 28. In general, a particle or space of irregular shape may still have a diameter defined. Four times the cross-sectional area divided by the wetted perimeter yields a formula for hydraulic diameter. Herein, by effective diameter is meant the hydraulic diameter in a situation where an actual single uniform diameter does not exist.

Meanwhile, each particle 16, 18, 20, 30 may also have an effective radius 27, and effective diameter 29, which characterize it. These radii 27 and diameters 29 may exist over a range of sizes within a single prill 10, or over several different prills 10. Meanwhile, prills 10, themselves, may be formed to have an effective radius 26 and diameter 28 of any suitable size.

For example, the size of a prill 10 may be selected to correspond to seed, fertilizer, or other material with which (or in the equipment for which) the prills 10 will be applied. This way, no change in process, no change in equipment, and no change in settings will need to be made in order to apply the prills 10 in an agricultural process. Thus, in one embodiment, calculations and measurements of application rates, delivery volumetric flows, and so forth may be easily determined and easily set on equipment for applying the prills 10 to a soil.

Thus, in general, each of the particles 16, 18, 20, 30 may be thought of as a generic particle 30. Thus, we may speak of all the particles 30, or any of the particles 30, or of specific types of particles 16, 18, 20.

Figure 2:
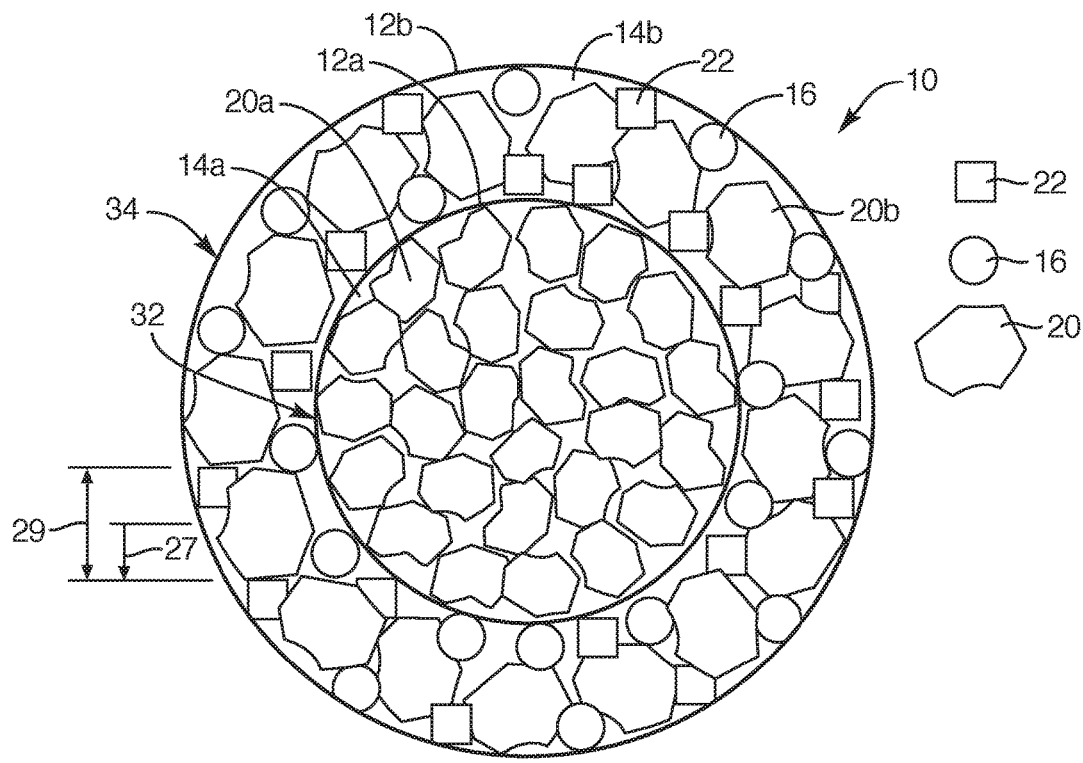
FIG. 2 is a schematic representation of an alternative embodiment of a layered prill.

Referring to FIG. 2, an embodiment of a prill 10 in accordance with the invention may be constructed in a layered configuration. For example, in the illustrated embodiment, an inner agglomeration 32 or an inner prill layer 32 or core 32 may exist. It may be formed by any of the processes by which the overall prill 10 is formed. However, the constituents of the inner agglomeration 32 may be different from those of an outer agglomeration 34. For example, an inner agglomeration 32 may be formed, with some binder 14 and various particles 30, such as the particles 20a. Thereafter, the inner agglomeration 32 may be added to with one or more outer agglomerations 34 or layers 34. These may include the same or different particles 20b. Meanwhile, either one or both of the agglomerations 32, 34 may include an appropriate amount of binder 14, nutrients 16, biocides 18, absorbents 20, a combination thereof, a sub-combination thereof, or the like. For example, in one embodiment the inner agglomeration 32 may be constituted by primarily nutrients 16 and biocides 18, with a comparatively lesser fraction of absorbents 20. Meanwhile, the outer agglomeration 34 may be constituted by primarily absorbents 20. In such an embodiment, the disintegration of the prill 10 from the outside first would sew the soil with the bulk of the absorbents 20 before the nutrients 16, biocides 18, or both are released. In this way, for example, the absorbents 20 in the outer agglomeration 34 would be first to be released from the binder 14, and thus be hydrated and ready to absorb the dissolved nutrients 16 and biocides 18, when those are dissolved from and released by the inner agglomeration 32.

Figure 3:
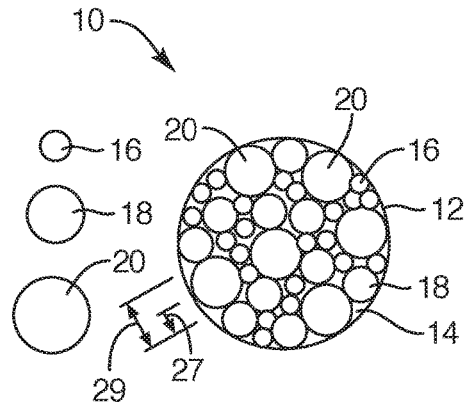
FIG. 3 is a schematic illustration representing an alternative embodiment of a single agglomeration in which constituents have disparate sizes.

Referring to FIG. 3, while continuing to refer to FIGS. 1-7 and FIGS. 1-15, generally, there is no fundamental requirement that nutrients 16, biocides 18, and absorbents 20 all be of the same size. There is also no fundamental prohibition thereagainst. Thus, in the illustrated embodiment the prills 10, in FIG. 3, particles 30 may be shown at widely disparate sizes. The schematics cannot even show just how widely the particles 30 may differ from one another in size, orders of magnitude in diameter or mass. Of course, even within one species, such as a single nutrient 16 or biocide 18, or even absorbents 20, a range of sizes may exist (e.g., by natural Gaussian distribution) within a constituent. On the other hand, constituents may instead be run through a system of sieves in order to assure a narrowing of the size distribution thereof.

Figure 4:
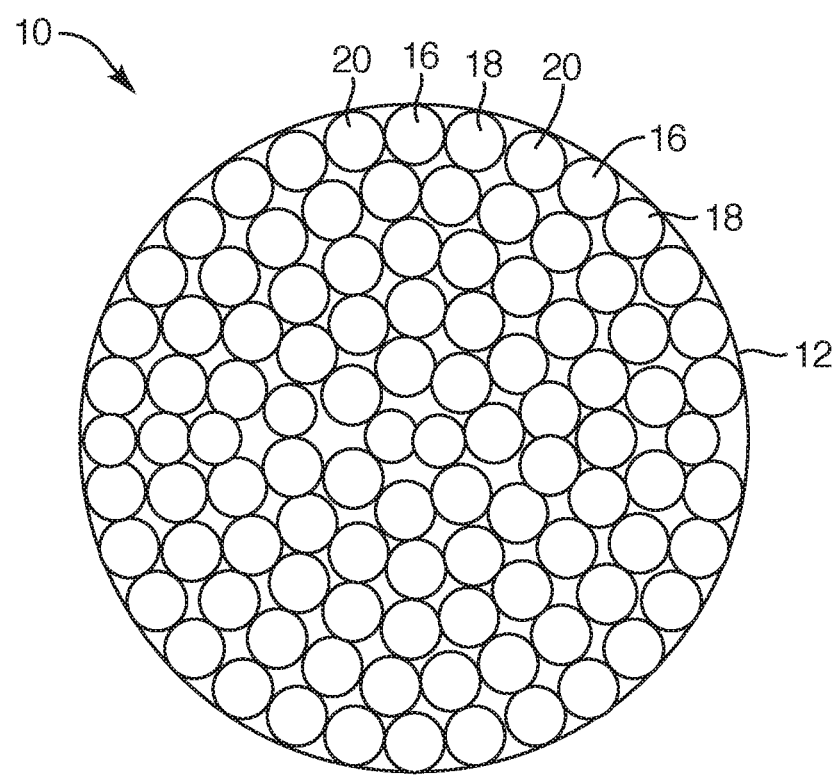
FIG. 4 is a schematic representation of an alternative embodiment of a prill in which the agglomeration includes a typical distribution of sizes of all constituents in about the same range for each.

Referring to FIG. 4, the particles 30 may be formed in such a way that nutrients 16, biocides 18, and absorbents 20 are all within the same comparatively close size range selected. This simplifies certain manufacturing processes. However, depending on the process, the sequence of events, whether a prill 10 is substantially homogenous or uniform in its distribution of constituents, whether it is layered, or the like, such parameters may vary. Size will typically be engineered value selected for or obtaining proper dissolving and dispersion rates of the key constituent.

Figure 5:
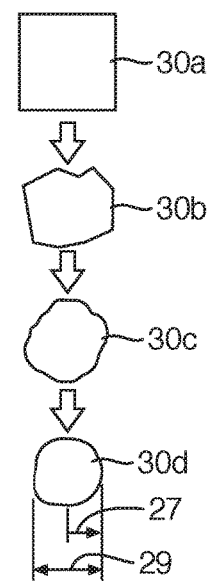
FIG. 5 is a schematic representation of the tendency of particles upon tumbling, mixing, or working to more closely approximate a sphere.

Referring to FIG. 5, a particle 30a may have any shape, including concavities, sharp corners, or the like. Nevertheless, by tumbling, processing, mixing, and even certain agglomeration or other manufacturing processes, most particles tend to be subject to rounding by the removal of corners. The particle 30b, with more processing, milling, tumbling, or the like, the breaking off of additional corners forms an even smoother particle 30c. Finally it is approximating a round, or almost round, particle 30d. Again, each of these may have an effective radius 27 and effective diameter 29 defined by hydraulic radius and hydraulic diameter.

Figure 6:
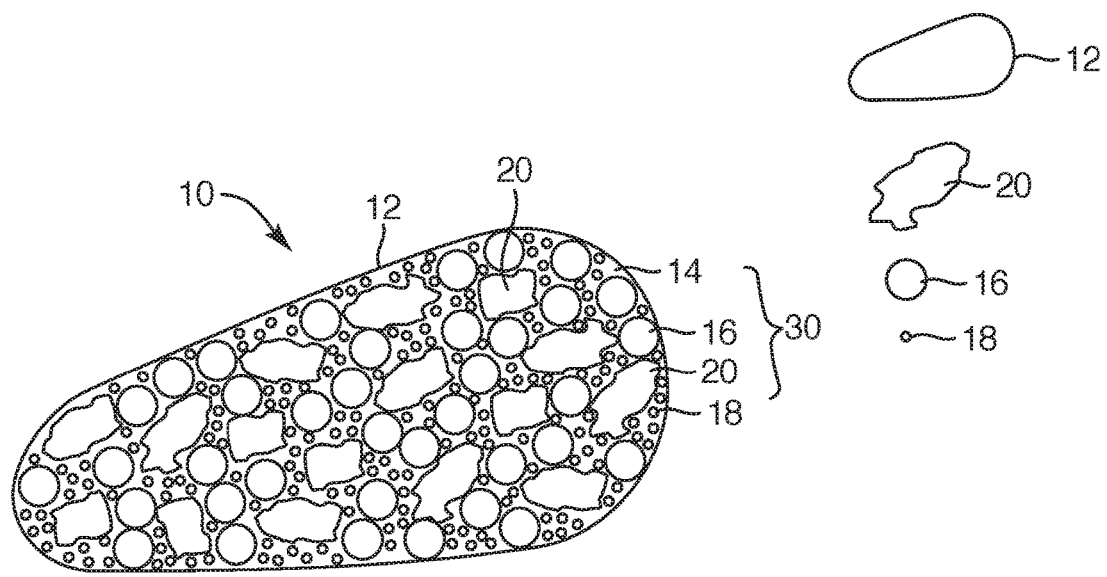
FIG. 6 is a schematic illustration of an alternative embodiment of a prill formed about a substrate.
Figure 7:
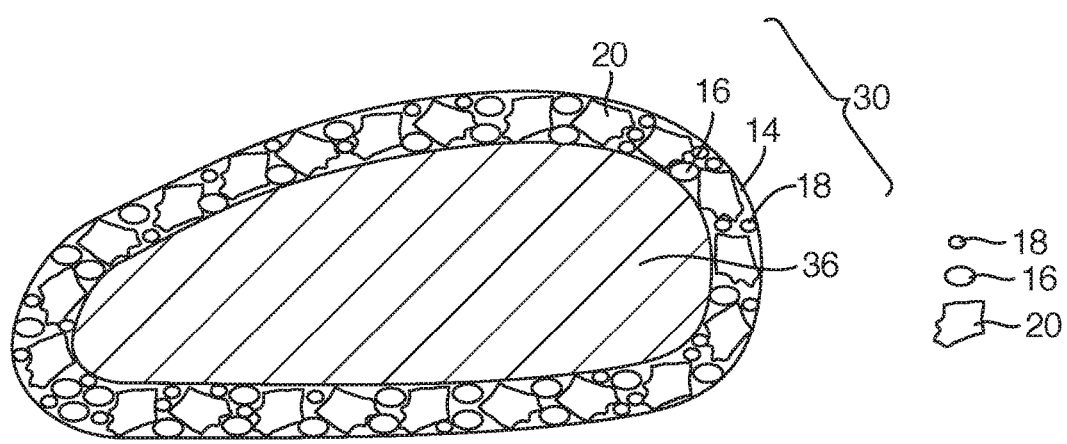
FIG. 7 is a cross-sectional view thereof, illustrating a substrate, such as a seed, forming the core of a prill.

Referring to FIGS. 6-7, while continuing to refer generally to FIGS. 1-15, a prill 10 may be formed on a substrate or "substrated." In the illustration, a binder 1 may secure nutrients 16, biocides 18, and absorbents 20 in, on, or forming the surface 12 of the prill 10. In the illustrated embodiment, the core 36 or substrate 36 will typically remain impervious to the additives, such as the binder 14, the nutrients 16, biocides 18, and absorbents 20.

Nevertheless, it is not necessary that every nutrient 16, every biocide 18, or any combination thereof be constituted as a solid particle 30. Rather, the availability of certain nutrients 16, biocides 18, and the like may be best as liquids. Such may be mixed into the binder 14 as a liquid, in order to provide greater flexibility in formulation and manufacture of prills 10. Thus, in the illustrated embodiment, some or all of the nutrients 16, some or all of the biocides 18, even a portion of an absorbent 20, or any combination thereof may be embodied in liquids mixed with or forming the binder 14. They may thus be applied to a substrate 36, or as a binder 14 generally in the embodiments of FIGS. 1-8.

Figure 8:
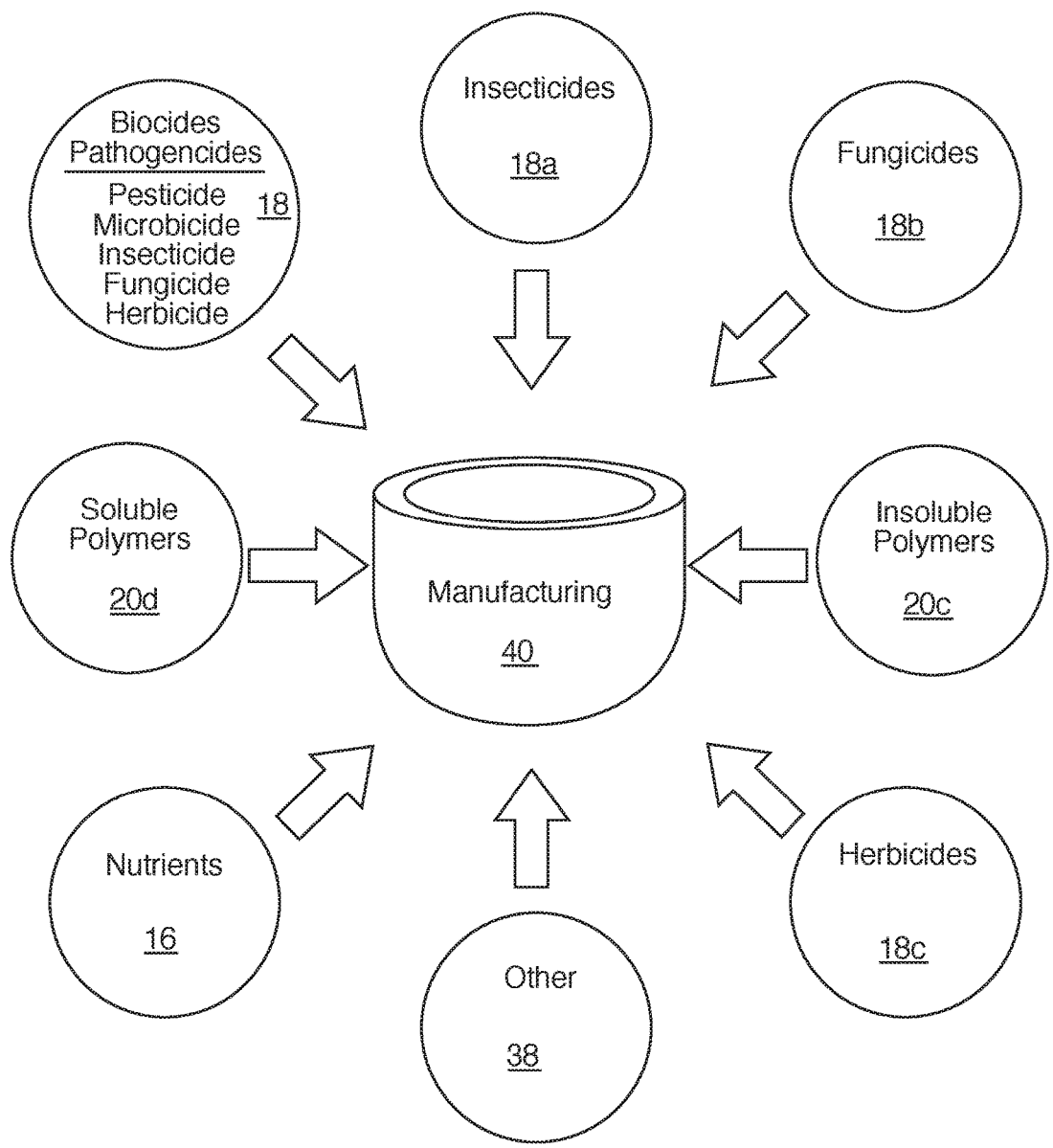
FIG. 8 is a schematic block diagram of a manufacturing process for combining various absorbents, biocides, nutrients, and binders.

Referring to FIG. 8, nutrients 16, various types of biocides 18, such as insecticides 18a, fungicides 18b, herbicides 18c, and so forth may be mixed together to form a prill 10. Similarly, various absorbents 20, such as insoluble polymers 20c and soluble polymers 20d may also be included in a prill 10. Again, biocides 18 may include any pathogencide, such as pesticides, microbicides, insecticides, fungicides, herbicides, and so forth. Nutrients 16 may include any nutrients, as well as any additives that may modify growth patterns.

Many other constituents 38 may be included. For example, materials to speed growth, inhibit growth, inhibit germination, accelerate germination, or the like may be discovered, or included from the litany of available agricultural products currently available. Thus, whether old or new, or yet to be discovered, various other constituents 38 may be included in the manufacturing 40 of prills 10.

Again, a composition and method in accordance with the invention may include any suitable combination of solid particles 30 and liquids in the binder 14 in order to accomplish the delivery of a prill 10 calculated to meet the specific needs of a particular application. In fact, one may optimize with suitable computer processing, formulation of a manufacturer of prills 10.

Figure 9:
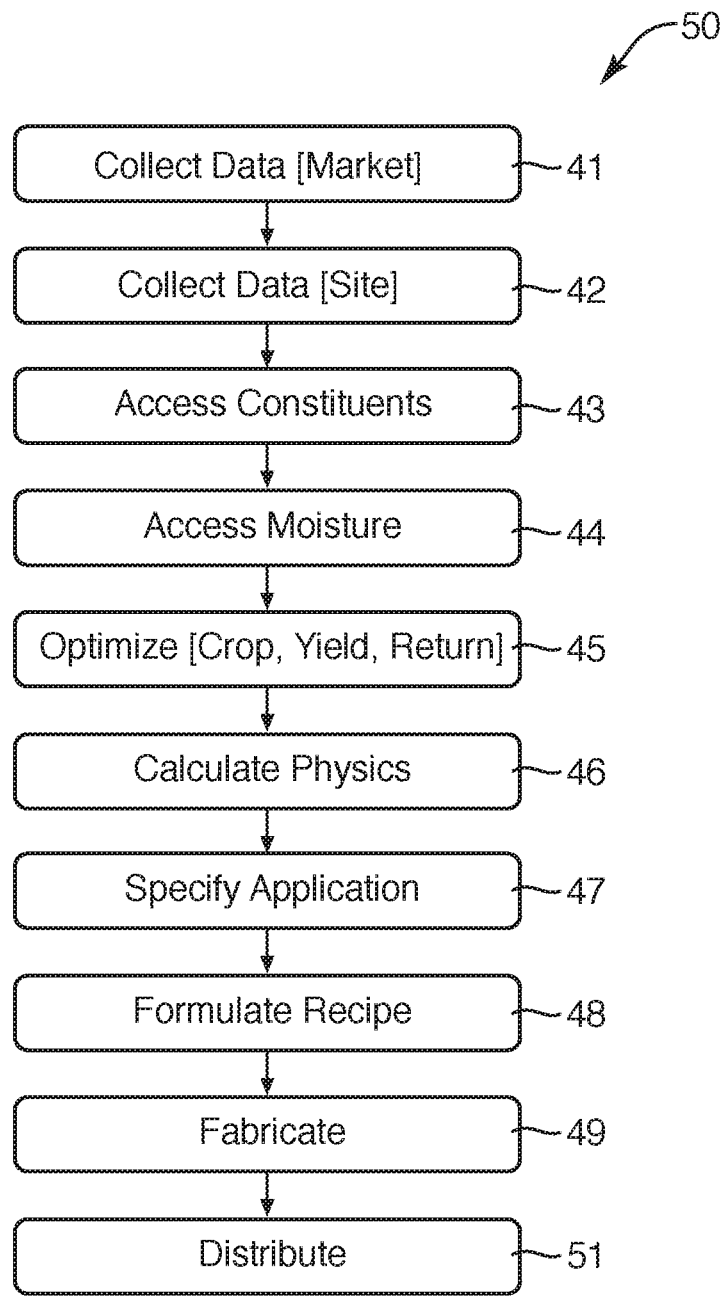
FIG. 9 is a schematic block diagram of a process for optimizing a prill design and the application process.

Referring to FIG. 9, for example, one may collect 41 data related to market information. For example, one may think of the crop varieties possible to be grown in a particular acreage on ground, a market for the yield of such crops, the proximity of that market, the typical payments in that market, whether calculated by averages, historical performance, values of futures, or even purchase of crops by a receiver of those crops. One may collect 41 such data and any other related to the market for a crop.

Meanwhile, collecting 42 data related to a site or a plot of ground, an acreage, a farm, or the like may provide various information about the available resources. These may include water from irrigation, water from rainfall, or other moisture, chemical composition of the soil by constituent, soil geology, such as clay, sand, loam, and so forth. Similarly, site data regarding drainage, and so forth may also be collected 42.

An assessment 43 or assessing 43 the constituents may be done by a computer analysis including all of the devices and methods that soil chemistry laboratories may use. Thus one may characterize a soil to its nature, water holding capacity, porosity, oxygenation, nutrients, and so forth. Thus, assessing 43 may involve a computerized analysis of the data in order to provide a clear output that characterizes the site from which the data was collected 42.

Likewise, assessing 44 moisture may involve weather analysis, climate analysis, irrigation analysis and so forth. Similarly, assessing 44 the moisture may also include analysis by computer models of the particulate size, chemical constitution, mechanical constitution (e.g. compaction, porosity, drainage) and so forth of the soil. In this way, assessing 44 the moisture situation of a site will assist in understanding how much water is available, how it flows through the soil, its final disposition, its tendency to evaporate, accumulate, flow away, leach out, and so forth.

Various optimization techniques exist. For example, the Simplex Method is a method whereby various constraints on a domain may be established, and an optimum found within the system. The Simplex Method is well understood in the arts of computer science and engineering. Meanwhile, various methods such as Newton's Method, the method of steepest descent, and various other optimization techniques are well established in the mathematical field of numerical methods, and the operational theory of optimization and so forth. Thus, any suitable optimization method may be used.

A computer may be programmed to take the assessment 43, also done by an assessment computer program (e.g., software), and the assessment 44 of the moisture situation, in order to optimize 45. The system may optimize a selection of crop, a yield of crop of that type, a return on the yield of that crop, and an assortment of nutrients 16, biocides 18, and absorbents 20 suitable to that crop and yield.

For example, it is not a foregone conclusion that more of anything is always better. Rather, optimizing 45 the crop, yield, and return, on the basis of a moisture assessment 44, constituent assessment 43, and the recommended content of a prill 10, or design of a prill 10 will permit a farmer or farm manager to specify exactly what will be put into production, such that no constituent is over matched or improperly matched with respect to another. All may be balanced, or moved closer to balancing by sowing an amendment prill.

For example, if more fertilizer or nutrients 16 would provide a better yield, but the necessary moisture content is not available, then outrunning the water supply with excess nutrients is not necessarily an optimum solution. Similarly, if moisture is plentiful, but will result in much leaching out of nutrients, then perhaps the timing of nutrients, the encapsulation or embodiment of the nutrients in a solid formation, or the like is in order. They may be optimized to provide time release from a solid. Their release in close proximity to an absorbent will effect the transport processes (an engineering expression for mass transfer) into water of the nutrients.

Meanwhile, nutrients from the absorbent 20, delivered there by the particles 30, and nutrients 16 and biocides 18, may be absorbed and stored with water in the absorbents. These may pass directly from the roots of the plant, or both.

In general, it has been found that the absorbents 20 may be formulated in a size of granularity that provides greatly increased surface area ratio to volume. The surface area-to-volume ratio is a function of effective diameter (hydraulic diameter). For example, the area of a circle is pi times radius (r) squared. The circumference is 2·pi·r. The volume of the sphere is $4/3\pi r$ cubed. The surface area of a sphere is $4\pi r^2$. Thus, in terms of diameter (d), circumference is $\pi d$, and the area of the circle is $\pi d2/4$. The volume is $1/6\pi d^3$. The area of a surface of a sphere is $\pi d^2$. Thus, optimization may ultimately include an output that will provide a recommended rate of application.

The development of the mathematics demonstrates that the ratio of the surface area of a particle to the volume of the particle varies inversely with six times the diameter. That is, area of the surface divided by the volume of the sphere equals one divided by six times the diameter.

One result is that the number of pounds per acre (kilograms per hectare) multiplied by the cubic feet per pound mass (density) provides the rate of how many cubic feet of material will be delivered per acre or how many cubic meters per hectare. Likewise the number of pounds per acre to be applied multiplied by the dollars per pound of constituent or prill equals the number of dollars per acre or dollars per hectare. This is the cost per acre for administering or applying an additive to the soil either as an individual constituent or as a prill.

The number of pounds per foot length (meter) of furrow may be determined by the number of rows and the length of the rows in each acre or hectare of ground. Thus the number of pounds or kilograms per foot or meter of furrow may be established. The acre may be divided up by its number of furrows or distance between furrows in order to establish the number of feet or meter of furrow per rate of area of the plot or plat. Thus, the pounds or kilograms per foot or meter of furrow multiplied by the cost per pound of product provides the cost per length of furrow required. This may be correlated with the application rate of seed.

The rate of dispersion, reaction, or other process at a boundary is a function of surface area. The size of particles may be established by the surface area to volume ratio. Thus, according to the formulas above, as diameter decreases, the surface area per volume of each prill 10 or each particle 30 increases at six times the rate of diameter change. Thus, the optimizing process 45 may benefit from calculating 46 the physics of absorption, holding, and release.

For example, the physics and chemistry of the particles 30 will provide a rate of release, and an amount of diffusion across the surface through a distance. Thus, Fick's law of diffusion (documented in the arts of heat transfer, mass transport, and the like) governs the diffusion of a chemical species at a concentration through an area of a medium. Thus, the calculating 46 of the physics will provide a recommendation for the ratio of area to mass (or area to volume) controlling the effective diameter of each particle 30, as well as that of the prill 10, itself.

Likewise, the calculation 46 or analysis 46 of the physics (that is, the physical operational parameters, whether engineering, mathematics, chemistry, or the like) will establish a suitable or preferred diameter, surface area, and the material properties for rates of diffusion, rates of absorption, and so forth. Accordingly, one may specify 47 an application by the rate of weight or volume of prills, and the amount of each constituent particle 30 within the prill including nutrients 16, biocides 18, absorbents 20, and binder 14.

The binder 14 may actually include some or all of the nutrients 16, biocides 18, or both. Meanwhile, the absorbents 20 may also absorb certain fractions of the nutrients 16, biocides 18, and so forth, whether from the particles 30 in which they reside as solids being dissolved by liquids in contact therewith, or from the binder 14 directly. Thus, a process 50 or system 50 may specify 47 the application of each of the constituents in a prill 10, and the amount of prill material to be applied in a furrow.

Formulating 48 a recipe includes determining by the mathematical and computer modeling thereof, the appropriate sizes, constituents, base materials, active chemicals, diffusion rates, distances, solubility, other rates and material properties, and so forth for each of the binder 14, nutrients 16, biocides 18, and absorbents 20.

Fabricating 49 may be done by any suitable method. For example, forming prills of fertilizer is well understood in the art. For example, Feeco International™ is a supplier of agglomeration machinery for use in manufacturing plants to manufacture prills 10. Engineering specifications and machinery are available directly from them.

Distributing 51 may include distributing prills commercially from a manufacturing plant to various distributors, as well as a distribution process to individual retailers, to individual farms, and ultimately sowing the prills in the ground with seed, or during cultivation. It is contemplated that sowing prills 10 at the time of sowing seed is the preferred method, as the most effective way to keep the prills 10 in close proximity to seeds. One may thus target very specifically in the same region, within a distance of inches or fractions of an inch, the prills 10 with respect to the seeds 36. That is, seeds may be part of prills, as substrates 36, or may simply be simultaneously sown therewith by a drill such as a grain drill, a broadcast spreader, or the like. A previous patent application Ser. No. 13/598,135, incorporated herein by reference, discloses methods for achieving broadcast effectiveness in coated seeds.

Figure 10:
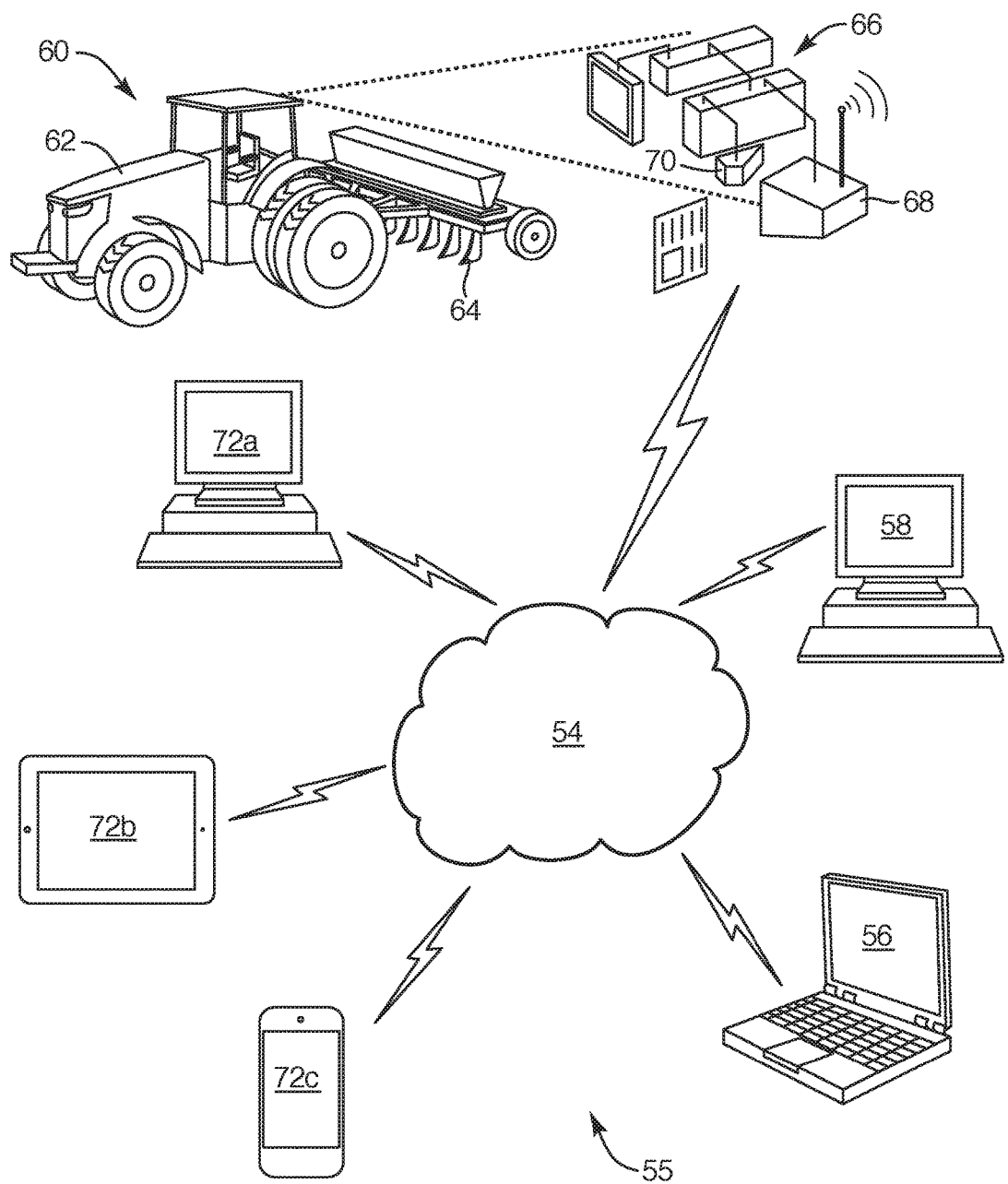
FIG. 10 is a schematic block diagram illustrating a process for optimizing prill design and application.

Referring to FIG. 10, while continue to refer generally to FIGS. 1-15, a process 50 may be implemented among a system of interconnected computers, including computers operating equipment on a farm or on a plot of ground, as well as laboratory equipment of others. For example, in the illustrated embodiment, over the internet 54, multiple computers may communicate. For example, a database computer 56 may be responsible for hosting database software that will accumulate data and store it for use by other computers within the system 55.

Likewise, an optimizer 58 may include one or more computers 58 responsible for conducting the optimizing 45 of the process 50, the calculating 46 or analyzing 46 of the physical realities of the chemistry, materials, material properties, and so forth. Likewise, the optimizer 58 may include one or more computers dedicated to specifying 47 the application rates based on the assessing 43, 44 of data 42 collected from the site of a plot, as well as the data collected 41 for the financial and other analyses based on markets.

Thus, each of the steps 41-51 in the process 50 may be implemented on one or more computers. The optimizer 58 may be thought of as the system 58 of computers 58 that analyze data, analyze the significance of that information, optimize materials and processes, and output or specify the decision as to what materials should be used to balance with one another in order to optimize the use of materials without wasting water, chemicals, absorbents, other additives, or the like.

Meanwhile, a delivery system 60 or system 60 may include a motive means 62, such as a tractor 62 drawing a dispersion device 64, such as a grain drill 64 or a seed drill 64. In the illustrated embodiment, the tractor 62, drill 64, or both may be equipped with computers systems 66, that may include controllers, readers, meters, servo-controls, feedback sensing, actuators, and so forth. Likewise, all the constituents of the computer, from monitors to processors, memory, and the like may exist within the system 66.

For example, sensors 70 may operate to sense levels of materials, rates of distribution, rates of flow, and so forth within the drill 64, on the tractor 62 over the ground, and so forth. Thus, the linear speed at which a tractor moves 62 and the rate of dropping by a drill 64 of seed 36 and prills 10 may all be observed by sensors 70. Meanwhile, a communication device 68 may communicate between the computer system 66, and the Internet 54 or any other computer connection thereto.

For example, various computers of 72a, 72b, 72c may be of a desktop type 72a, a mobile tablet type 72b, a portable hand held device 72c, or the like. Thus, a farmer, an equipment operator, a farm manager, a production manager, an analyst, or other person may rely on one of the computers 72 to download information from the database computer 56. They may apply optimization techniques, such as those used by an optimizer 58, or other analysis techniques in order to analyze, predict, control, direct, and otherwise effect the proper distribution, allocation, rate control, and the like of distribution 51 of prills 10 on a plot of ground.

Figure 11:
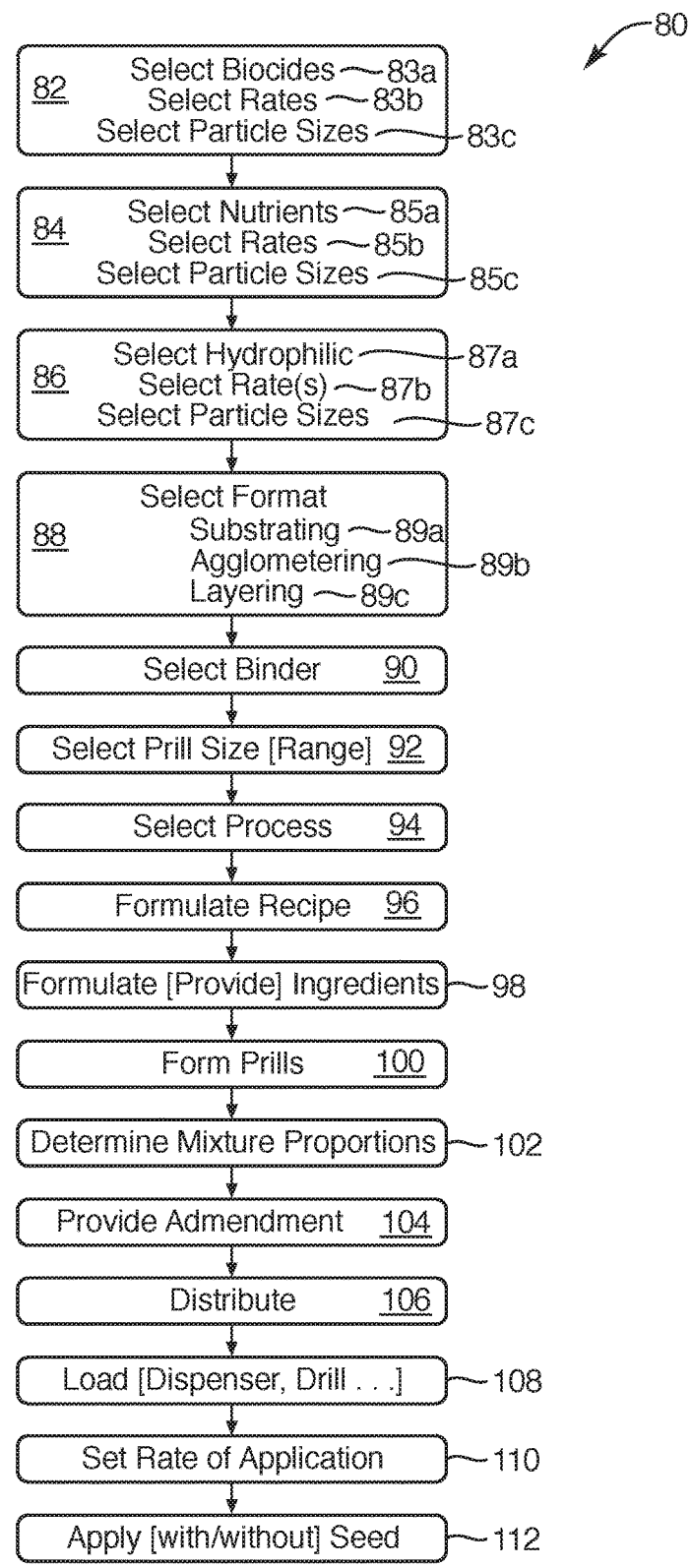
FIG. 11 is a schematic block diagram of a process for manufacturing a prill in accordance with the invention.

Referring to FIG. 11, in one embodiment of a process 80 in accordance with the invention, selecting 82 may include selecting 83a biocide, selecting 83b a respective rate of distribution, and selecting 83c a particle size. By selecting 83 is not necessarily meant grabbing a number from a look-up table although that may be done at the time of application. Typically, selecting 83 requires prior analyzing, and recommending, based on that analysis. Thus, the selection of step 82 for biocides may be executed for multiple biocides that are indicated for use by the assessment 43 of the process 50.

Similarly, selecting 84 nutrients may be conducted for multiple nutrients 16. For example, selecting 85a a specific nutrient, selecting 85b the respective rate of application, and selecting 85c a particle size may be done for each specific nutrient 16. Several may be deemed necessary, based on the assessment 43 of the constituents in the soil and the constituents that may be properly added.

Similarly, selecting 86 a hydrophilic material 20 or an absorbent 20 may include selecting 87a the specific chemical species or composition, selecting 87b the rate of application, and selecting 87c a particle size. These may all include analysis of the physics of absorption and release of water, absorption of various species of chemicals that may be constituted within the binder 14, nutrients 16, biocides 18, or the like, and so forth.

Selecting 88 a format may depend on analysis of the nature of nutrients 16, biocides 18, and the binder 14. For example, substrating 89a may involve coating sand, seed, organic materials, or something else that will be suitable as a carrier. Likewise, agglomerating 89b may involve agglomeration of very small particulates 30 into prills 90 in one of the forms discussed hereinabove, or another means. Likewise, layering 89c is a process corresponding to FIG. 2 wherein one or more constituents may be applied in one or more layers. These may each constitute the same or different constituents or particles 30 and proportions thereof.

Ultimately, analysis and selecting 90 a binder 14 will typically correspond and depend from to the longevity desired for the prill 10 to exist as a prill 10. In certain experiments, it has been found that prills 10 may disintegrate promptly in a matter of minutes. They may thus release smaller particles of absorbents 20 in a soil nearby. Nevertheless, because of the mechanical size of those particles 30 of absorbents 20, the absorbents 20 cannot migrate any great distance through the interstices in the soils but over long times (days, weeks) or by cultivation. Great surface area may be selected and available for the absorbents 20, and may be also available for the nutrients 16, biocides 18, or any combination thereof.

Selecting 90 a binder involves analyzing what would be in the binder and what particular binder properties are necessary. Likewise, selecting 92 a prill size may be based on an analysis of the flow through an application device 64, such as a drill 64, and may correspond to the type of seed being dropped as well. It is also governed by dispersion activity as it disintegrates, constituents and sizes, and so forth.

Likewise, selecting 94 a process for manufacture 40 may be done in cooperation with providing 96 a recipe. For example, the specific recipe will have an effect on the manufacturing 40. Liquids will affect the agglomeration processes of fabrication 49. Meanwhile, more or less liquid may need to be added, and certain of the solid constituents shown here such as nutrients 16, biocides 18, or the like may alternatively be constituted as liquids, thus altering the recipe provided 96.

Likewise, providing 98 or formulating 98 the ingredients will depend on the analysis done before. This is typically that associated with the formulating and providing the recipe after providing 96 and the recipe.

Finally, forming 100 the prills 10 is the physical process of conducting the agglomeration of manufacturing 40 discussed hereinabove. Thereafter, one may determine 102 mixture proportions, provide 104 the amendment to the soil through the selection of prills, the amounts, application rates and so forth, and distribute 106 the prills through a commercial chain. In this instance, distributing 106 does not include all that the distributing step 51 includes.

For example, here, commercially distributing 106 will eventually result in delivering prills in bags 130a, boxes 130b, totes 130b, or the like to a farm where loading 108 a drill will be coordinating with setting 110 a rate of application, and actual applying 112 the prills 10 with or without seed 36. For example, prills 10 may be sown as part of cultivation. However, sowing provides a single device 64 for delivery of the soil amendments 10 and the seed 36 as separate granules, but in a single operation. Meanwhile, sowing is effective at keeping prills 10 and their constituents in very close proximity to seeds 36, in accordance with the invention, if they are both drilled with the same drill 64, at the same time.

Figure 12:
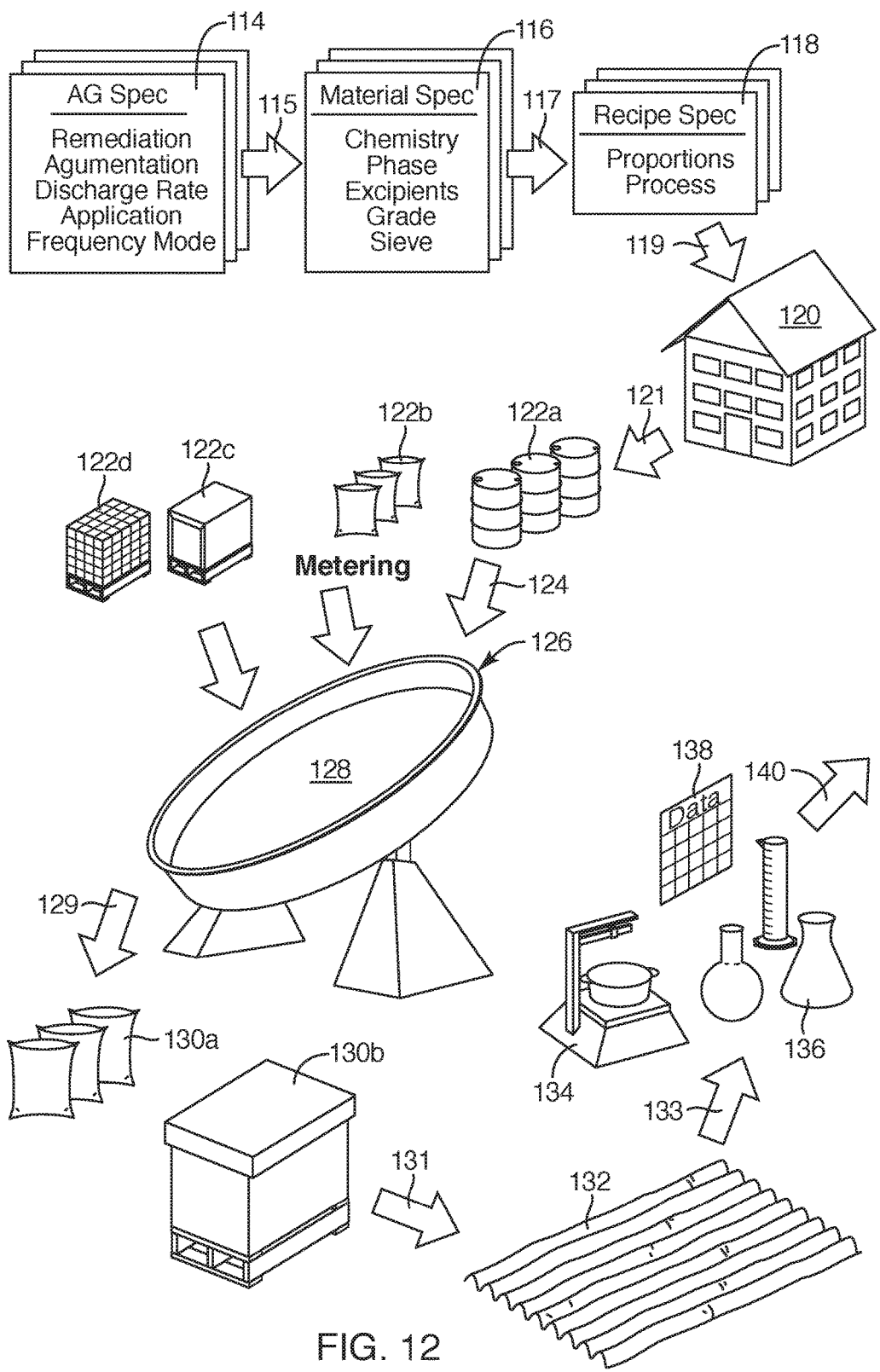
FIG. 12 is a schematic block diagram of a process from specification of constituents through manufacturing, application, data collection, and analysis of the results of application of prills in accordance with the invention.

Referring to FIG. 12, in one embodiment of a process 80, providing 113 certain input data as described hereinabove may result in an agricultural specification 114. That specification 114 may specify the result of the assessment 43 of constituents in the ground and those amendments (e.g., constituents of prills 10) that should be added. It typically includes the assessment 44 of moisture available, and that which should be held by various augmentation mechanisms, such as the absorbents 20 of the prills 10.

For example, ground may require remediation of soil conditions or chemistries, augmentation or addition of materials, and so forth. Remediation may include removal of salts, neutralizing salts, and the like with compounds of sulfur, and the like. Meanwhile, discharge rates, application rates, frequency, mode of distribution, and the like may be determined by computer optimization and output as part of an agricultural specification 114. The Agricultural specification 114 is the result of assessing 43 the constituents of the soil, and those which may be added for any purpose or removed, as well as assessing 44 the moisture and condition throughout the season.

Thus, providing 115 the specification 114 results in development of a material specification 116. This includes the material chemistry, the phases (e.g., solid, liquid, vapor) whether soluble, any excipients, such as bulking materials, weighting materials, space-takers, and any other materials that may be needed to process the prills 10. The specification 114, 116 permit a process to engineer the behavior of prills 10 from the time of formulation through application and in-situ operation. For example, chemistry, material phase, the excipients, the grades of any of the foregoing or other materials or properties, the sieve, sizes, and the like will go into the materials specification 116. One may think of the process 50 when optimizing 45 and calculating or analyzing 46 the physical behavior, that the materials specification 116 corresponds to the output of specifying 47 the application of materials to agricultural ground.

Meanwhile, the materials specification 116 is provided 117 to create a recipe specification 118. The recipe specification 118 is directed specifically to proportions of the specific ingredients, and the processes for combining them to provide the proper physical characteristics that will accomplish the formation of prills, distribution thereof, application thereof, and operation of the constituents in those prills 10 after hydration in the ground.

Thus, the recipe specification 119 is provided to manufacturing 120 which then outputs 121 the materials in various formats 122. For example, barrels 122*a*, bags 122*b*, pallets or totes 122*c*, or the like may be provided to and filled by the manufacturing process 122*b*. Next, metering 124 of all of the containers 122 or the materials of the containers 122 in a granulation process 126 requires employment of an apparatus 128 such as a granulator 128, or one of the agglomeration devices 128 described hereinabove.

The output 129 of the granulator 128 is the prills 10 in a product 130*a*, 130*b* such as a bag 130*a* of prills 10 a tote 130*b*, such as a Gaylord 130*b*, or the like. Thus, the product 130 will be delivered 131 to a farming operation for use in an agricultural process, such as seeding and drilling at the beginning of the season, cultivating or fertilizing later, or the like. Thereupon, application 132 or applying 132 the product 130 to the plot will result in the prills 10 being sown with the seed 36 in one of the currently contemplated embodiments.

Ongoing physical analysis 134 of soils, crop yields, and the like may include weighing, counting, and the like as well as other physical analysis 134. For example, certain crops will be evaluated for their product quantity, content, and quality. Whether food, fiber, or the like, physical analysis 134 may provide insights into the quality (e.g., chemistry, sugar, texture, protein, etc.) of a crop yield, its quantity (e.g., weight per area, volume, length, etc.) and so forth. Meanwhile, other analysis, such as chemical analysis 136 may provide the nutrient value, the presence of certain constituents, and so forth resulting from the soil amendments 10 sown with the seed.

All of the analysis 134, 136, as well as the basic data collected 133 from the plot of ground will result in data 138 or analysis data 138 that provides information corresponding to (and disclosing) the effectiveness of the prills 10. A report 140 output to a user will help in formulating new specifications 114 corresponding to the subject plot, possibly a new material spec 116, recipes 118, manufacturing 120, and so forth.

Figure 13:
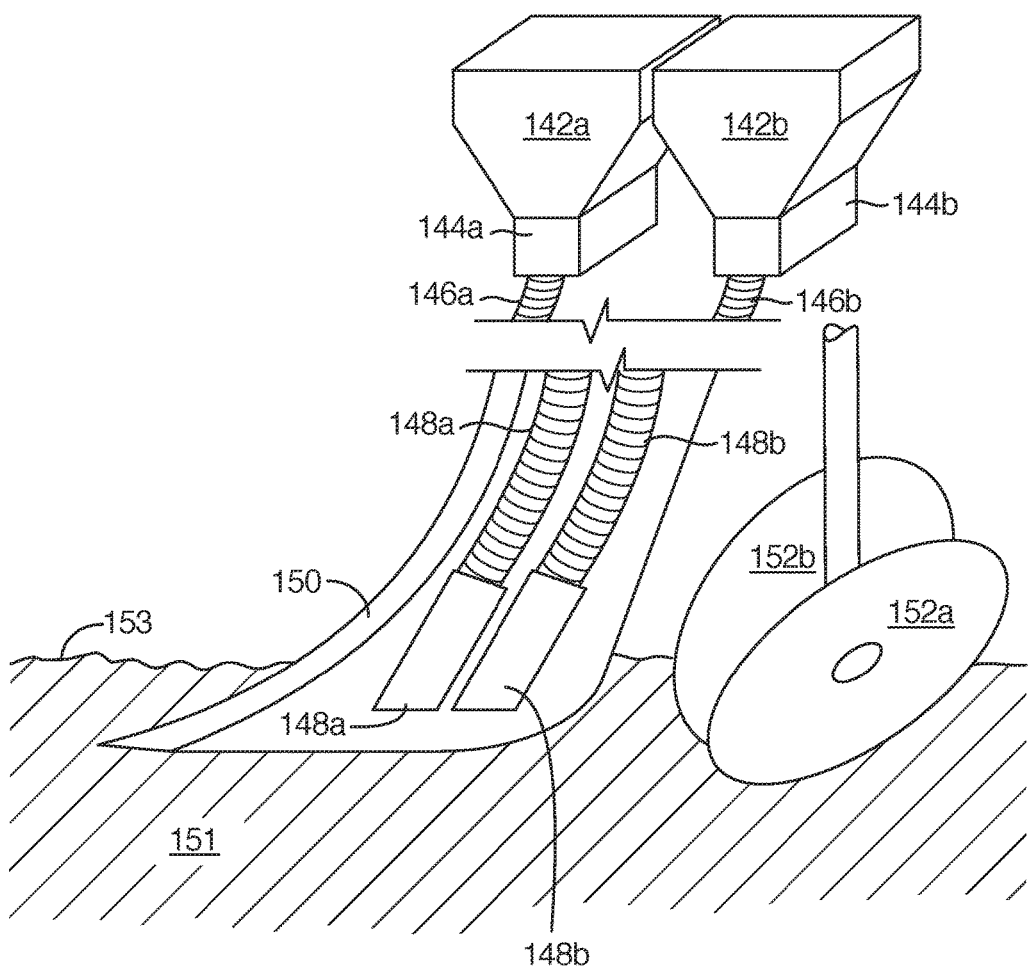
FIG. 13 is a side, elevation, partial cross-sectional view of a drill applying seed and prills simultaneously.

Referring to FIG. 13, application may be done by any suitable method. However, it has been found that minimizing the number of operations in agriculture reduces cost. Thus, if a grain drill or other drill will sow seed, whether by drilling, broadcasting, or the like, prills 10 may be distributed by the same mechanism, and possibly by the same actual device, even at the same time, or any or all in any combination.

In one embodiment illustrated, a hopper 142*a* may be filled with seed, and another hopper 142*b* may be filled with prills 10. Each may have its own metering device 144*a*, 144*b*, respectively, feeding into a conduit 146*a*, 146*b*, respectively for drilling. Typically, each conduit 146*a*, 146*b* will descend to within the envelope (spatial volume) defined by a shoe 150 of the drill 64 penetrating the ground 151 to extend under the surface 153 thereof. Accordingly, ports 148*a*, 148*b* will drop the seed 36 and prills 10, respectively into the ground 151.

Typically, a covering device 152 may follow the shoe 150, thus covering any furrow dug by the shoe 150. Typically, discs 152*a*, 152*b*, may continuously move soil from its position away from the seed to a position over the seed. Likewise, a drag 152, a chain, a bar, a harrow, or the like may be used as a closure device 152. In some embodiments, prills 10 may be mixed in a single hopper 142*a* with seeds 36. Seeds 36 may form the core of a prill 10.

Figure 14:
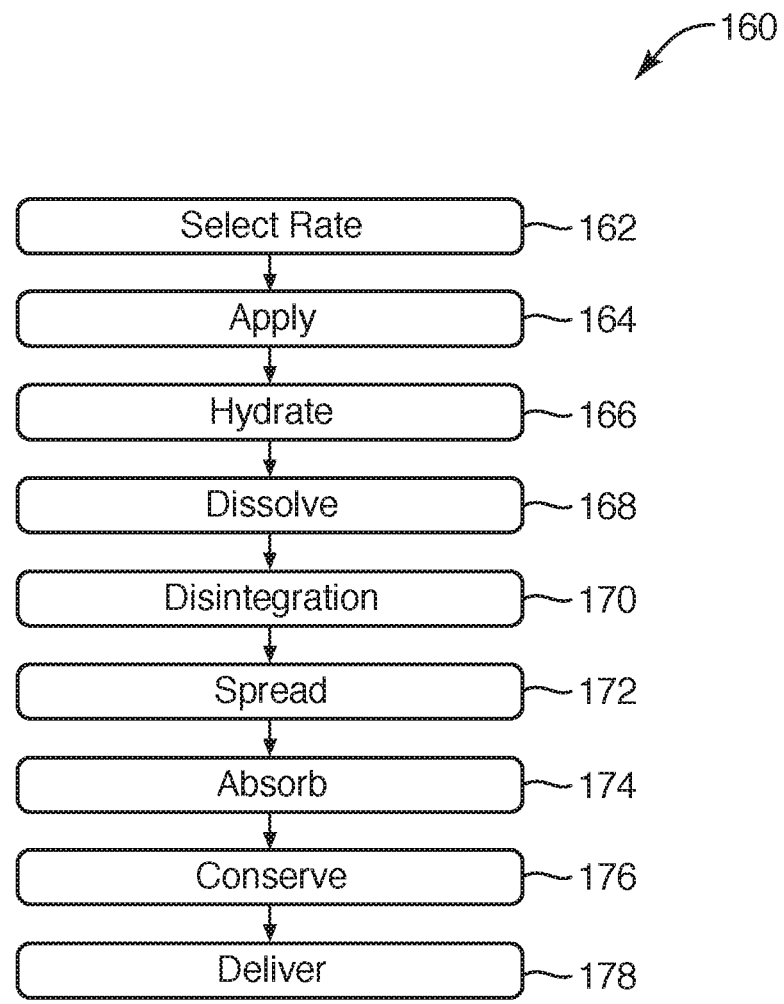
FIG. 14 is a schematic block diagram of the operational process of the prill supply, including each individual prill, operating subsequent to a manufacturer, from application to delivery of constituents to the subject plants.
Figure 15:
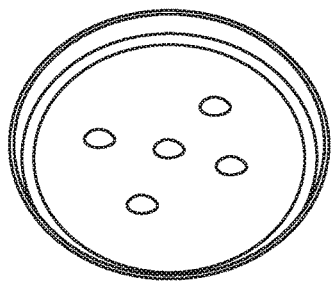
FIG. 15 is an illustration of operation of prills upon hydration, such as occurs after application to soil.
Figure 15:
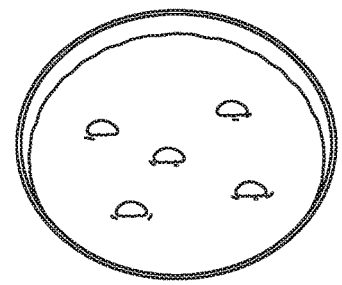
Figure 15:
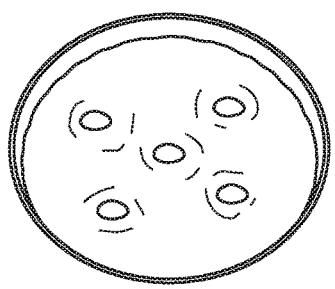
Figure 15:
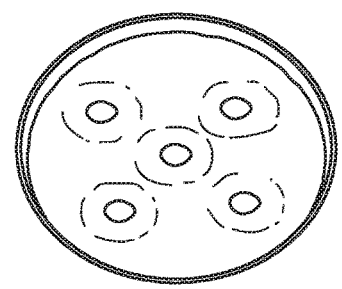
Figure 15:
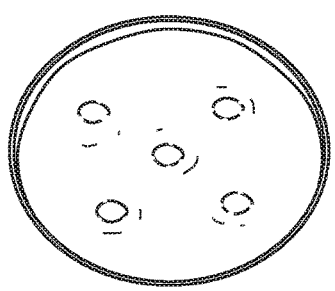
Figure 15:
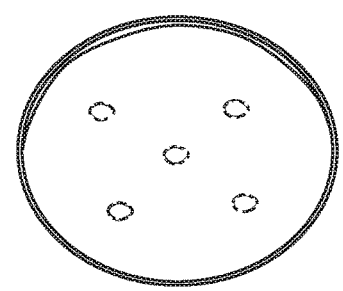
Figure 15:
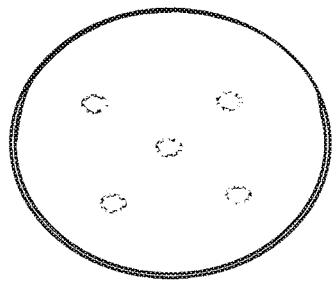
Figure 15:
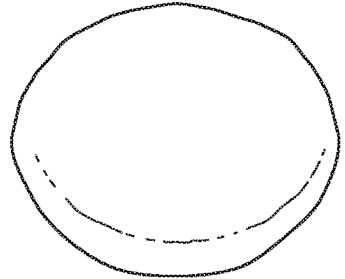

Referring to FIG. 14, operation of the prills 60 has been engineered and tested in experiments to determine the operational characteristics, the benefits of sizing the particles 30 agglomerated within each prill 10, and so forth. In one embodiment of a process of operation of the prills 10, the method 160 or process 160 may include selecting 162 a rate of application.

Selecting 162 rates of application has been described hereinabove for application by pounds per acre or kilograms per hectare, as well as mass per linear length of furrow. Thus, the selecting 162 of a rate of application may be corresponded with the rate of distribution of seed. Applying 164 the prills has been described with respect to FIG. 13, and elsewhere. Thus, hydrating 166 may involve irrigation, rainfall, or any natural or artificial means.

Water coming into contact with the prills 10 will dissolve 168 the binder 14, resulting in disintegration 170 of the prills in certain embodiments. This is in contradistinction to other inventions, even of the instant inventors of this application which may resist disintegration 170 intentionally. In the case of prills 10 here, disintegration 170 is a benefit. Thus, spreading 172 by the constituents within disintegrating prills may occur as described hereinabove.

Specifically, the particles 30 of absorbents 20 will be able to spread 172 somewhat as permitted by the mechanics of the soil, yet each remain autonomous and integral. Each particle 30 of absorbent 20 may swell with the absorption of water, and shrink with dehydration. Still, the individual particles 30 of absorbents 20 may spread comparatively slowly but in the vicinity of the seed, in the furrow where both have been sown. Thus roots will reach those particles 30 of absorbents 20.

Absorbing 174 of water by the absorbents 20 will be coincident with absorption 174 by the absorbents 20 of biocides 18 and nutrients 16 dissolved 168 in the water. That is, the binder 14 dissolves 168 in order to release all the particles 30 contained in a prill 10. Meanwhile, certain solid materials or liquids, by way of nutrients 16, biocides 18, or both, may also begin to dissolve 168 into the same water that is dissolving in the binder 14. Thus, absorbing 174 by the absorbents 20 includes absorbing the water, which is held by for its own sake as hydration for the plants, as well as nutrients 16 and biocides 18 dissolve in that water.

Absorbing 174 amounts to scavenging 174 by the absorbents 20, the nutrients 16, biocides 18, and the like in the immediate vicinity. Forming a prill 10 with all of these constituents 30 within it, including the binder 14, any liquid nutrients 16 and liquid biocides 18, and well as any solid nutrients 16 and solid biocides 18 in close contact with the absorbents 20 provides for ready absorption 174. This will be true of any liquidous material contacting the absorbents 20. With the water, they will be held by the absorbents 20 for uptake by roots that later access the absorbents 20 for their water content.

Thus, the particles 30 of absorbents 20 conserve 176 or maintain 176 a store of nutrients 16, biocides 18, and water therein. Accordingly, when touched by a root fiber capable of absorbing water, the prills 10, now disintegrated 170 into their constituent particles 30, such as the absorbents 20, deliver 178 the nutrients 16 and biocides 18 to the roots of the plants. Certain materials may be engineered to leach to a greater or lesser extent into the surrounding soils to eradicate pests, whether of the animal kingdom or plant kingdom, in order to protect a seed 36 or plant growing from a seed 36 sown with the prills 10. That is the operational principle of any biocide may be maintained in operation to best effect its purpose.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for amending soils and promoting plant growth, the method comprising:
   providing a custom blended prill that comprises a first constituent containing at least one component selected from the group consisting of:
   a first nutrient,
   a first protectant, and
   a polymer capable of retaining water;
   selecting a first binder effective for coating the first constituent;
   agglomerating the first binder and the first constituent into prills comprising a first layer;
   providing a second constituent containing at least one component selected from the group consisting of:
   a second nutrient,
   a second protectant, and
   a polymer capable of retaining water;
   selecting a second binder effective for coating the second constituent;
   agglomerating the second binder and the second constituent into a second layer on the prills;
   the first constituent and the second constituent include different components and the prill includes at least one protectant; and
   providing the prills for application to the portion of soil.

2. The method of claim 1, further comprising:
   coating the prills with an excipient selected to urge the prills to feed properly through machinery designed to do at least one of spreading fertilizer, sowing fertilizer, spreading seed, or sowing seed.

3. The method of claim 2, further comprising:
   inserting at least a portion of the prills into the portion of soil to be amended.

4. The method of claim 1, wherein the prills have an effective prill diameter selected so as to allow effective distribution in the portion of soil that is to be amended.

5. The method of claim 1, wherein the prill has an effective prill diameter selected so as to feed through a seed drill without modification thereof.

6. The method of claim 1, wherein the first constituent is a liquid nutrient that is mixed into the first binder.

7. The method of claim 1, wherein the second constituent is a liquid protectant that is mixed into the second binder.

8. The method of claim 1, wherein the first constituent contains at least two components selected from the group consisting of a first nutrient capable of enhancing plant growth, a first protectant capable of reducing the effectiveness of pathogens attacking plants, and a water absorbent polymer capable of retaining water.

9. The method of claim 1, wherein the first constituent contains at least two components selected from the group consisting of a first nutrient capable of enhancing plant growth, a first protectant capable of reducing the effectiveness of pathogens attacking plants, and a water absorbent polymer capable of retaining water and the second constituent contains at least two components selected from the group consisting of a first nutrient for enhancing plant growth, a first protectant capable of reducing the effectiveness of pathogens attacking plants, and a water absorbent polymer capable of retaining water.

10. The method of claim 1, wherein the first and second binders are water soluble.

11. A method for amending soils and promoting plant growth, the method comprising:
    providing a prill that comprises a first constituent containing at least one component selected from the group consisting of:
    a first nutrient,
    a first protectant, and
    a polymer capable of retaining water;
    selecting a first binder effective for coating the first constituent;
    agglomerating the first binder and the first constituent into prills comprising a first layer;
    providing a second constituent containing at least one component selected from the group consisting of:
    a second nutrient,
    a second protectant, and
    a polymer capable of retaining water;
    selecting a second binder effective for coating the second constituent and;
    agglomerating the second binder and the second constituent into a second layer on the prills;
    wherein the first constituent and the second constituent include different components.

12. The method of claim 11, further comprising:
    coating the prills with an excipient capable of facilitating the prills to feed properly through machinery designed to do at least one of spreading fertilizer, sowing fertilizer, spreading seed, or sowing seed.

13. The method of claim 11, further comprising:
inserting at least a portion of the prills into a portion of soil to be amended.

14. The method of claim 11, wherein the prill has an effective prill diameter selected so as to feed through a seed drill without modification thereof.

15. The method of claim 11, wherein the first constituent is a liquid nutrient that is mixed into the first binder.

16. The method of claim 11, wherein the second constituent is a liquid protectant that is mixed into the second binder.

17. The method of claim 11, wherein the first and second binders are water soluble.

18. A method for amending soils and promoting plant growth, the method comprising:
providing a prill that comprises a first constituent containing at least two components selected from the group consisting of:
a first nutrient capable of enhancing plant growth,
a first protectant capable of reducing the effectiveness of pathogens attacking plants, and
a polymer capable of retaining water;
selecting a first binder effective for coating the first constituent;
agglomerating the first binder and the first constituent into prills comprising a first layer;
providing a second constituent containing at least two components selected from the group consisting of:
a second nutrient capable of enhancing plant growth,
a second protectant capable of reducing the effectiveness of pathogens attacking plants, and
a polymer capable of retaining water;
selecting a second binder effective for coating the second constituent;
agglomerating the second binder and the second constituent into a second layer on the prills;
the first constituent and the second constituent include different components; and
coating the prills with an excipient selected so as to urge the prills to feed properly through machinery designed to do at least one of spreading fertilizer, sowing fertilizer, spreading seed, or sowing seed.

19. The method of claim 18, further comprising:
inserting at least a portion of the prills into a portion of soil to be amended.

20. The method of claim 18, wherein the first and second binders are water soluble.

* * * * *